United States Patent [19]

Flemming et al.

[11] Patent Number: 4,829,233

[45] Date of Patent: May 9, 1989

[54] MICROWAVE PROBE

[75] Inventors: Michael A. Flemming, Abingdon; Graham N. Plested, Didcot, both of United Kingdom

[73] Assignee: United Kingdom Atomic Energy Authority, London, England

[21] Appl. No.: 164,470

[22] Filed: Mar. 4, 1988

[30] Foreign Application Priority Data

Mar. 9, 1987 [GB] United Kingdom ............... 8705463
Jan. 22, 1988 [GB] United Kingdom ............... 8801395

[51] Int. Cl.$^4$ ..................... G01N 22/04; G01R 27/26
[52] U.S. Cl. ............................. 324/58.5 C; 324/58 C
[58] Field of Search ............... 324/58 R, 58 A, 58 B, 324/58 C, 58.5 R, 58.5 B, 58.5 A, 58.5 C

[56] References Cited

U.S. PATENT DOCUMENTS

| | | |
|---|---|---|
| 3,509,456 | 4/1970 | Zurbrick . |
| 3,581,197 | 5/1971 | Morey . |
| 3,750,013 | 7/1973 | Rotman . |
| 3,942,107 | 3/1976 | Gerhard . |

FOREIGN PATENT DOCUMENTS

| | | | |
|---|---|---|---|
| 0082560 | 12/1982 | European Pat. Off. . | |
| 86/06495 | 11/1986 | PCT Int'l Appl. . | |
| 0842514 | 6/1981 | U.S.S.R. | ......................... 324/58.5 C |
| 1322131 | 7/1987 | U.S.S.R. | ......................... 324/58.5 C |

| | | |
|---|---|---|
| 1354474 | 5/1974 | United Kingdom . |
| 1480629 | 7/1977 | United Kingdom . |
| 2048492 | 12/1980 | United Kingdom . |
| 2129944 | 5/1984 | United Kingdom . |

OTHER PUBLICATIONS

Chang: "Varactor Tuned Microstrip Ring Resonators'-'-IEEE Intl. MW Symposium-1986.

Itoh: "A New Method for Measuring Properties of Dielectric Materials Using a Microstrip Cavity".

Primary Examiner—Reinhard J. Eisenzopf
Assistant Examiner—Jose M. Solis
Attorney, Agent, or Firm—William R. Hinds

[57] ABSTRACT

A microwave probe for determining properties of a fluid medium, and particularly for separating measuring dielectric constant and dielectric loss, comprises an insulating substrate metallized on one face, an electrically isolated, ring-shaped, resonant element defined on the opposite face, and shielded means to couple microwaves into and from the element such that the element can undergo a resonance. The resonant frequency depends on the dielectric constant of an adjacent medium, while the Q-factor of the resonance depends on the dielectric loss of the medium. In one method of operation microwaves are coupled into the element to force an oscillation, and the driving frquency is varied to obtain a resonance.

10 Claims, 3 Drawing Sheets

MICROWAVE PROBE

The invention relates to a probe utilizing microwaves to determine properties of a medium adjacent to or surrounding the probe.

The use of microwaves to sense and measure properties such as moisture content of materials is well known, this being based on measurement of the dielectric properties of the material under test. Typically the dielectric constant and/or the dielectric loss depend upon the material or the condition of the material being tested. For example, many industrially significant dry materials have low dielectric constants and low dielectric loss. The presence of even small amounts of moisture can cause significant changes in both these parameters since, in the microwave frequency region, water has both a high dielectric constant and a high dielectric loss. The dielectric properties of water also show resonant effects which depend on the manner in which the water is bound to the support material.

A typical method of measurement involves passing a microwave beam through the substance under test and measuring the magnitude, and sometimes the phase, of the transmitted and/or reflected signals. This method suffers errors due to spurious reflections which are dependent on sample geometry, positioning and surface condition. Another method is to place the sample in some form of resonant cavity and measure the effect on the resonant frequency or Q-factor of the cavity. This method usually requires a specially shaped sample and is rarely suited to on-line industrial monitoring.

For industrial use, consideration has been given to probes which can be inserted into or placed against the surface of the product. These probes can take the form of microwave aerials, open ended transmission lines or 'leaky' transmission lines. The microstrip line is an example of the last type mentioned above. A microstrip line consists of a narrow printed conductor on one side of a dielectric substrate, the opposite face of which is metallised. A microwave signal may be transmitted along the microstrip in a similar manner to transmission on a co-axial transmission line but, in microstrip, the electric and magnetic fields are only partially contained within the substrate, because the printed conductor is not wholly shielded. The 'fringing field' outside the substrate may interact with another material brought into contact with the substrate and this forms the basis of the microstrip type of sensing probe. The advantages of this type of probe include ease of use in on-line applications an, because the electromagnetic fields are guided along the substrate, freedom from spurious reflections from sample discontinuities located away from the microstrip.

For example GB No. 1 354 474 (N.R.D.C.; M. Kent) describes an apparatus for determining the dielectric properties of materials comprising an enclosure through which the material may be passed, the enclosure enclosing part of a length of a strip line. Microwave energy is applied to and received from the length of strip line. The material being tested comes into close proximity with the strip line, but has to be in a form suitable for passing through the enclosure. M. Kent and T. E. Price in "Compact Microstrip Sensor for High Moisture Content Materials" (Journal of Microwave Power, 14(4), 1979) describe a compact and robust microstrip probe which can be placed in contact with a material such as a liquid which is to be tested. The probe comprises a U-shaped strip conductor with terminals at each end, embedded in a polytetrafluoroethylene/glass substrate, sandwiched between two metal ground planes except at the part acting as the probe where there is a metal plane at only one side of the substrate. On insertion of the probe into a sucrose solution the attenuation of the microwave energy is an increasing function of the moisture concentration. It is however difficult to relate the measured results to the properties of the test sample and, in particular, it is difficult to determine the relative effects of dielectric constant and of dielectric loss on the microstrip transmission parameters.

According to the present invention there is provided a fluid characterising apparatus comprising a probe immersible in a fluid to be characterised, the probe comprising an electrically insulating substrate, with a substantially continuous conducting layer, and an electrically isolated, ring-shaped resonant element separated by the substrate from the conducting layer, shielded means for causing microwaves to propagate in the element, and shielded means for sensing microwaves so propagating, the causing and sensing means being coupled to the element sufficiently weakly to have negligible effect on the natural resonance of the element, and such that if the probe is immersed in the fluid then part of the electromagnetic fields due to microwaves propagating in the element extend into the fluid, so that the fluid affects the resonant response of the element.

It will be appreciated that there must be intimate contact between the probe and the material to be characterised. The term fluid should therefore be understood as encompassing liquids and gases, and also powdered solid material. The causing means enables a microwave resonance in the element to be set up, this resonance occurring at one of a number of resonant frequencies, and the sensing means enables such a resonance to be detected. The coupling both between the causing means and the element, and between the element and the sensing means must be as weak as possible, so as to load the element as little as possible; the coupling capacitance should be the minimum for which the propagating microwaves can still be detected, for example the coupling capacitance might be in the range 20–30 fF, which provides adequate coupling for microwaves of frequency 10 GHz.

The element is preferably circular, but might be oval or elliptical. Such an element will resonate at those frequencies for which the perimeter of the element is an integral number of wavelengths. Because the element has no ends, the nature of the resonance is simplified, as there are no end effects. Another advantage of the ring-shaped element is that less microwave power is radiated from the element than would be the case with a straight resonant microstrip element. The element is desirably of low resistance, to minimize energy loss in the element itself. Furthermore it is preferably of uniform width to further minimize complexity in the resonances.

The microwaves may be coupled to and from the element by narrow conducting strips separated from the conducting layer by the substrate and terminating within a short distance (about a millimeter) of the element, the distance being such that microwaves are capacitively coupled across it, each such strip being shielded by a covering layer of insulating material and a shielding conducting layer. Alternatively and preferably the microwaves are coupled to and from the element by conductors extending normal to the conducting layer and terminating at an aperture in the layer adjacent to a portion of the resonant element but separated from it by the substrate. This ensures that the coupling electromagnetic fields are entirely within the substrate, and so the coupling is not affected by any media adjacent to the probe. These conductors may be the cores of coaxial cables, whose sheaths are connected to the conducting layer.

In one mode of use of the probe, microwaves are coupled into the resonant element and the microwave frequency is scanned through a natural resonance. The amplitude of the microwaves in the element is sensed at each frequency, so that both the resonant frequency (i.e. the frequency at which the amplitude is greatest) and the breadth of the resonance can be determined. Both these parameters depend upon the nature of the medium adjacent to the resonant element and into which the fringing fields from the element extend. The resonant frequency depends upon the dielectric constant (relative permittivity) of the medium; while the Q-factor of the resonance, i.e. the ratio of the resonant frequency to the band-width at half the peak power, depends upon the dielectric loss of the medium. This method of measurement thus enables these two dielectric parameters of the medium to be measured separately.

The invention will now be further described by way of example only and with reference to the accompanying drawings, in which:

FIGS. 1a and c show plan views of different probes;

FIG. 1b shows a sectional view on the line B—B of FIG. 1a;

FIG. 2. shows a block diagram representing an electrical circuit incorporating the probe of FIGS. 1a and b;

Figure 1A:
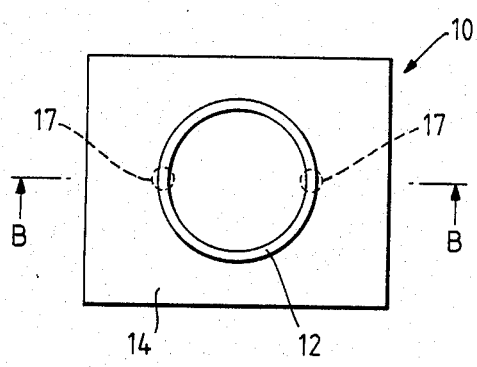
Figure 1B:
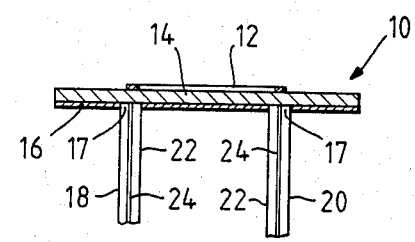

Referring to FIGS. 1a and b, these show a probe 10 including a resonant micro-strip element 12 in the form of a circular ring-shaped copper strip of mean diameter 33 mm on the front surface of a rectangular insulating substrate 14 of polytetrafluoroethylene (PTFE)/glass fibre laminate with a layer of copper 16 covering the rear surface. Two small circular holes 17 are defined in the layer 16 underneath diametrically opposed points on the resonant element 12. Two copper-sheathed, PTFE-insulated, coaxial cables 18 and 20 extend normal to the rear surface of the substrate 14, each terminating in one of the holes 17, with its sheath 22 soldered to the copper layer 16 around the edge of the hole 17. The core 24 of each cable 18 and 20 thus abuts the rear surface of the substrate 14, and is separated from the resonant element 12 only by the thickness of the substrate 14. The coupling capacitance between the end of each core 24 and the element 12 is only about 20 fF.

Figure 1C:
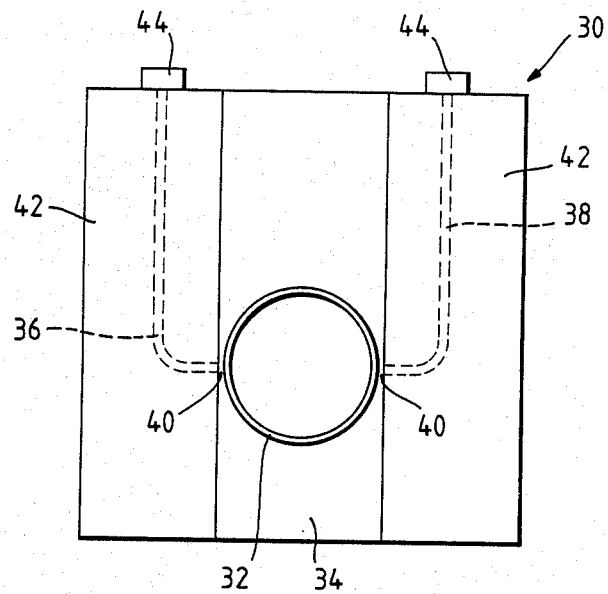

Referring to FIG. 1c, an alternative probe 30 includes a resonant micro-strip element in the form of a circular copper ring 32 on the front surface of a rectangular insulating substrate 34 of polytetrafluoroethylene/glass fibre laminate with a layer of copper (not shown) covering the rear surface. Copper strips 36 and 38 coplanar with the ring 32 extend radially away from two diametrically opposite points, being separated from the ring 32 by narrow gaps 40 each 1.0 mm wide. The strips 36 and 38 extend in a curved path to one edge of the substrate 34 where each is connected to a respective coaxial cable connector 44. Each strip 36 and 38 is completely covered by a further layer of the substrate material (not shown), itself covered by a second layer of copper 42. The connector 44 ensures both the rear copper layer and the copper layer 42 are earthed.

Thus each probe 10 and 30 includes an electrically isolated resonant ring-shaped micro-strip element 12 or 32; and means 18 and 20, 36 and 38 whereby microwave signals may be coupled into the resonant element or coupled from it, each of which is shielded to prevent leakage of microwaves, by sheaths 22 or copper layer 42. The coupling means 18, 20, 36 and 38 are preferably of characteristic impedance 50 ohms to match standard generating and measuring equipment; the resonant microstrip elements 12 and 32 might be of rather narrower microstrip with characteristic impedance in the range 50 to 100 ohms. The narrower the microstrip defining the element 12 or 32 the more precisely determined is its circumference, and hence the more sharply defined is the resonance; but on the other hand the narrower the microstrip the greater is the resistance, and hence the broader the resonance. For the element 12 of mean diameter 33 mm the optimum microstrip width is about 1 mm, which provides a characteristic impedance of about 80 ohms. Each probe 10 and 30 can be immersed in a liquid or powdered solid under test; in the case of the probe 30 the connectors 44 are preferably above the surface of the material under test. The resonant elements 12 and 32 might if desired be covered by a protective insulating layer, preferably of the same material as the substrate. Probe 10 might be modified by soldering coaxial cable connectors (similar to the connectors 44 of FIG. 1c) in the holes 17, to which the coaxial cables 18 and 20 could then be connected.

Figure 2:
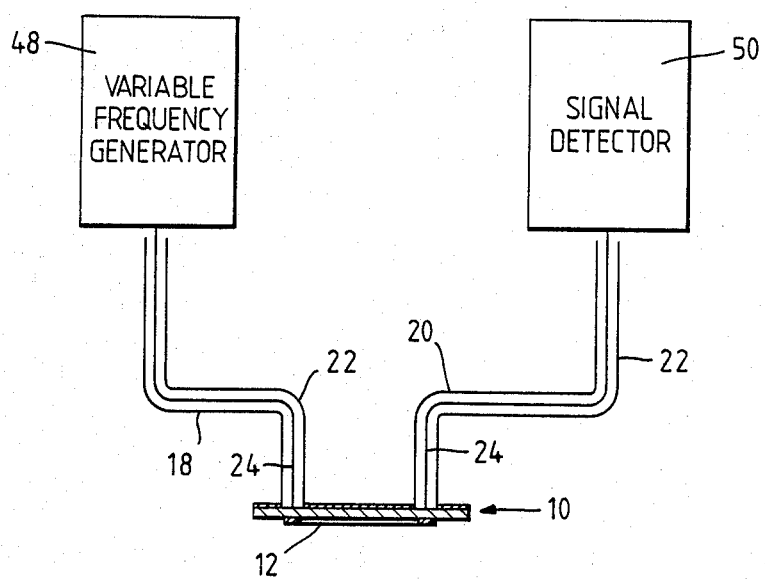

Referring to FIG. 2 there is shown diagrammatically a circuit for use with the probe 10, but which could equally well be used with the probe 30. As shown, one coaxial cable 18 is connected to a variable frequency generator 48 for generating microwave signals (for example between 1 and 20 GHz). The other coaxial cable 20 is connected to a microwave signal detector 50. The sheaths 22 of the cables 18 and 20 are both earthed.

Figure 3:
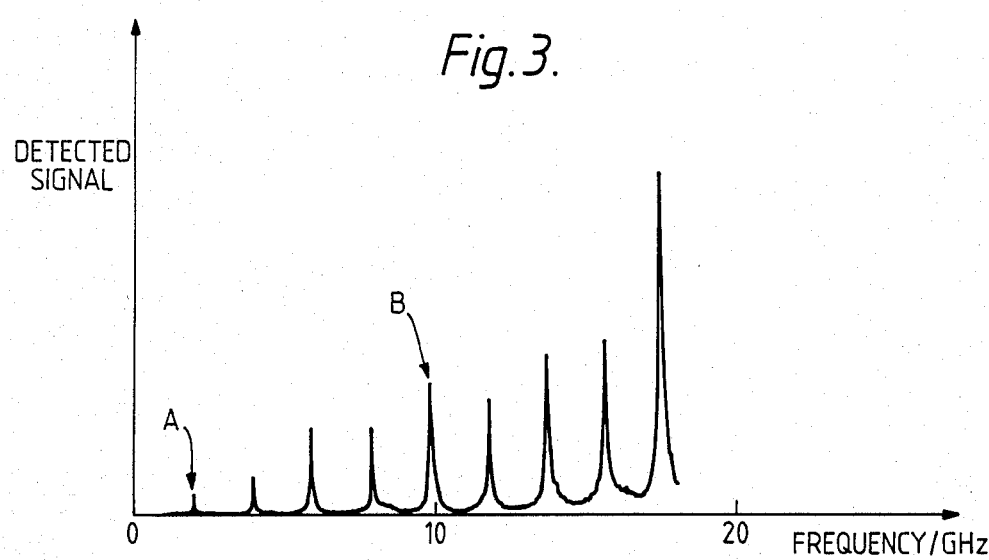
FIG. 3 represents graphically the variation of microwave amplitude with frequency in the circuit of FIG. 2 when the probe is adjacent to air.

Referring also to FIG. 3 there is shown the experimentally determined variation of detected signal with frequency for the circuit of FIG. 2 with air adjacent to the probe 10. Microwave signals generated by the generator 48 are capacitively coupled from the core 24 of the cable 18 into the resonant element 12, in which forced microwave oscillations therefore occur. The amplitude of the forced oscillations determines the amplitude of the signal coupled into the core 24 of the cable 20 and hence the signal detected by the detector 50. Because the coupling capacitance is small, the element 12 is not significantly loaded by the impedances of the generator 48 or the detector 50. For most frequencies the forced oscillation is of small amplitude, but for frequencies which correspond to the fundamental natural resonant frequency of the element 12 or a harmonic of it, the oscillation is of large amplitude. In this case the frequency was gradually increased from 1 GHz to 18 GHz. The fundamental resonant frequency A is seen to be about 2.0 GHz, and other harmonic resonances occur at frequencies which are integral multiples of that frequency. In general the amplitude of the oscillation increases as one goes to higher harmonics, principally because the coupling to and from the element increases with frequency. At the peak of the fifth resonance, B, approximately 0.15 of the voltage supplied by the generator 48 is received by the detector 50; the coupling is preferably such that this proportion does not exceed 0.2.

Figure 4:
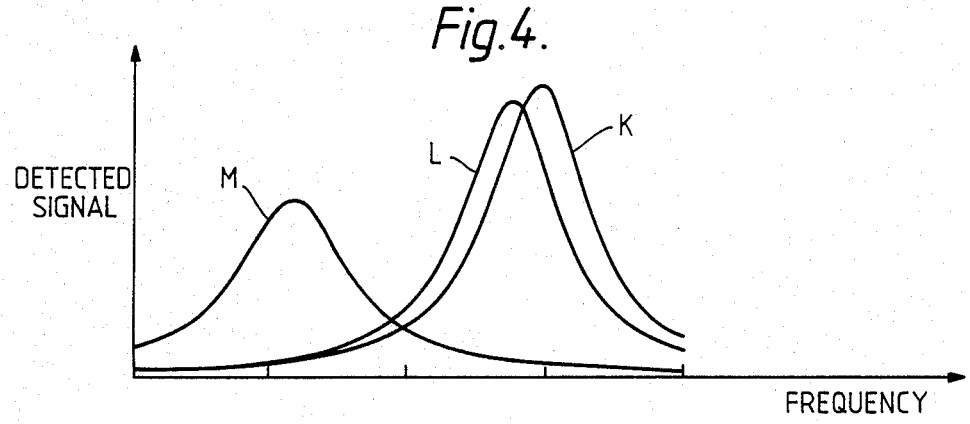
FIG. 4 represents graphically the variation in microwave resonance in the circuit of FIG. 2 when the probe is adjacent to different water-in-oil emulsions.

In practical use of the probe 10 it is only necessary to observe one such resonance. In FIG. 4, to which reference is now made, is shown graphically the fifth resonance (corresponding to that marked B in FIG. 3) for three different liquids adjacent to the resonant element 12: dry oil (graph K), 2% water/oil emulsion (graph L), and 10% water/oil emulsion (graph M). It will be observed that the increasing concentration of water in the emulsion leads to a decrease in the resonant frequency—because water has a higher dielectric constant than oil at these frequencies—the resonant frequency with 10% water/oil emulsion being 2% less than that with dry oil. There is also a decrease in the height of the peak amplitude and an increase in the width of the resonance peak—because water has a higher dielectric loss than oil at these frequencies—such that the Q-factor for the resonance (the ratio of the resonant frequency to the bandwidth at half the peak power) decreases from about 98 for dry oil to about 82 for 10% water/oil emulsion.

Figure 5:
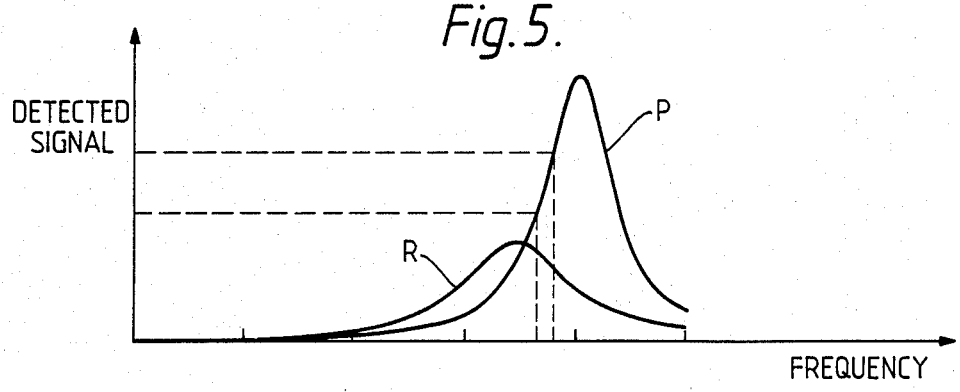
FIG. 5 represents graphically the variation in microwave resonance in the circuit of FIG. 2 when the probe is adjacent to different petrol/ethanol mixtures.

Similar results are obtained with other mixtures containing a component differing significantly in either dielectric constant or dielectric loss from the other component, and in FIG. 5 is shown the fifth resonance for two different liquids: pure petrol (graph P) and petrol with 10% ethanol (graph R). Here again it is observed that the addition of ethanol to the petrol leads to a decrease in the resonant frequency and to a decrease in the Q-factor of the resonance.

It will thus be appreciated that probes such as those of FIGS. 1a and b or FIG. 1c can be used in a circuit as indicated in FIG. 2 to measure dielectric properties of a medium. Equally they can be used to measure concentrations of one component (such as ethanol) in another (such as petrol), whether the components are miscible or form an emulsion.

It will also be appreciated that the probes might be used in a different manner to that described above; for example the microwave frequency might be modulated about a frequency near a resonant frequency, rather than being scanned through a resonance. This enables both the magnitude of the detected signal at that frequency, and the rate of change of detected signal with frequency (i.e. the gradient of the detected signal against frequency graph) at that frequency, to be detected. These two parameters enable the dielectric constant and the dielectric loss of the medium to be determined. In FIG. 5, and referring to graph P, if the frequency of the microwaves is modulated between the two values indicated by the broken lines, then the detected signal is clearly modulated in amplitude; the detected signal consequently has a dc component corresponding to its mean magnitude, and an ac component corresponding to the gradient of the graph.

Figure 6:
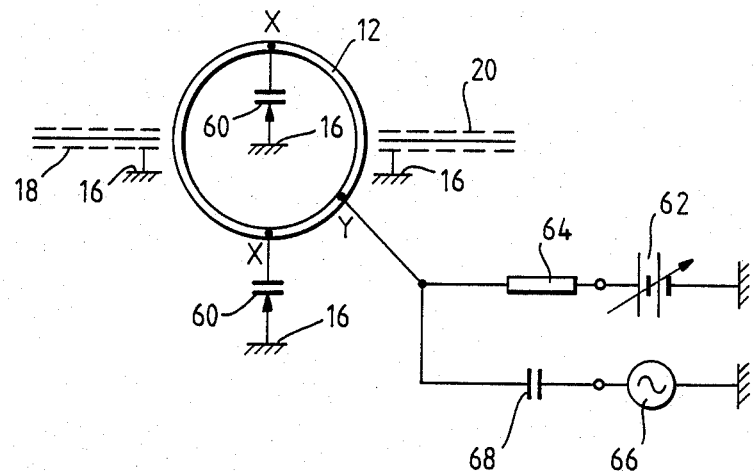
FIG. 6 shows diagrammatically a modified version of the probe of FIGS. 1a and b.

An analogous effect may also be achieved by modulating the electrical parameters of the resonant element itself so as to modulate its resonant frequency. Referring now to FIG. 6, this may be achieved by connecting two varactors 60 (i.e. reverse biased diodes whose capacitance is voltage-dependent) between the earthed copper sheet 16 and two diametrically opposite points X on the element 12 midway between the input and the output. At a position Y midway between the output and one point X are connected to the element 12 a source 62 to provide a dc bias voltage through a resistor 64, and an ac source 66 to provide a modulating voltage through a blocking capacitor 68.

In operation microwaves are coupled into the element 12 from the cable 18 at a constant frequency. The bias voltage is adjusted (typically up to 30V) to ensure that the second resonance of the element 12 is near to the frequency of the microwaves. Consequently there is an antinode of electric field at X, maximizing the effect of the varactors 60 on the response, and a node at Y, minimizing the effect of the components 62, 64, 66 and 68 on the response. An ac modulating voltage is then supplied by the source 66, so modulating the capacitance of the varactors 60 and hence the resonant frequency of the element 12. The signal in the cable 20 will consequently be modulated, its ac component being indicative of the gradient of the detected signal against frequency graph. As discussed above, from the values of the mean signal and the gradient the dielectric constant and dielectric loss of the material adjacent to the probe 10 can be determined.

We claim:

1. A fluid-characterising apparatus comprising a probe immersible in a fluid to be characterised, the probe comprising an electrically insulating substrate, with a substantially continuous conducting layer, and an electrically isolated, ring-shaped resonant element separated by the substrate from the conducting layer, shielded means for causing microwaves to propagate in the element, and shielded means for sensing microwaves so propagating, the causing and sensing means being coupled to the element sufficiently weakly to have negligible effect on the natural resonance of the element, and such that if the probe is immersed in the fluid then part of the electromagnetic fields due to microwaves propagating in the element extends into the fluid so that the fluid affects the resonant response of the element.

2. An apparatus as claimed in claim 1 wherein the causing means and the sensing means each comprises a shielded conductor extending normal to the conducting layer and terminating at an aperture in the conducting layer adjacent to a portion of the resonant element but separated from it by the substrate.

3. An apparatus as claimed in claim 2 wherein the apparatus also comprises a variable frequency microwave generator, and means for determining from the sensed microwaves a resonant frequency and a Q-factor of a resonance of the probe, and hence characterising the fluid.

4. An apparatus as claimed in claim 2 wherein the apparatus also comprises a frequency-modulated microwave generator, and means for determining from the sensed microwaves the mean amplitude, and the amplitude of the modulation in amplitude, and hence characterising the fluid.

5. An apparatus as claimed in claim 2 wherein the probe also comprises a varactor connected to the resonant element, the apparatus comprises a constant frequency microwave source, means for applying an alternating electrical signal to the varactor so as to modulate the resonant frequency of the element, and means for determining from the sensed microwaves the mean amplitude, and the amplitude of the modulation in amplitude, and hence characterising the fluid.

6. An apparatus as claimed in claim 5 wherein the probe comprises two varactors each connected to the conducting layer, and connected to respective positions on the resonant element at which, at a desired frequency of operation, there are antinodes of electric field.

7. A method of characterising a fluid comprising the operations of immersing a probe in fluid, the probe comprising an electrically insulating substrate, with a substantially continuous conducting layer, and an electrically isolated, ring-shaped resonant element separated by the substrate from the conducting layer, shielded means for causing microwaves to propagate in the element, and shielded means for sensing microwaves so propagating, the causing and sensing means being coupled to the element sufficiently weakly to have negligible effect on the natural resonance of the element, such that part of the electromagnetic fields due to any microwaves propagating in the element extends into the fluid, causing microwaves to propagate in the element, sensing the microwaves so propagating, and from the sensed microwaves characterising the fluid.

8. A method as claimed in claim 7 comprising the operations of causing microwaves of a plurality of different frequencies near to a resonant frequency to propagate in the element, determining from the sensed microwaves the resonant frequency and the Q-factor of the resonance, and hence characterising the fluid.

9. A method as claimed in claim 7 comprising the operations of causing microwaves of a frequency near to a resonant frequency to propagate in the element, modulating the frequency of the microwaves, determining from the sensed microwaves the mean amplitude, and the amplitude of the modulation in amplitude, and hence characterising the fluid.

10. A method as claimed in claim 7 wherein the probe also comprises a varactor connected to the resonant element, the method comprising the operations of causing microwaves of a constant frequency near to a resonant frequency to propagate in the element, and applying an alternating electrical signal to the varactor so as to modulate the resonant frequency of the element.

* * * * *